United States Patent [19]

Harvey

[11] Patent Number: 5,254,095
[45] Date of Patent: Oct. 19, 1993

[54] VEIN TENTER

[76] Inventor: Clyde B. Harvey, P.O. Box 1144, Monrovia, Calif. 91016

[21] Appl. No.: 888,507

[22] Filed: May 27, 1992

[51] Int. Cl.⁵ .................. A61M 5/00; A61M 5/32; A41F 1/00; A44B 1/04
[52] U.S. Cl. .................................... 604/115; 604/116; 604/177; 606/158; 606/210; 24/563
[58] Field of Search ........ 606/151, 157, 158, 205–210; 604/115, 116, 177–178, 192; 128/226; 24/563

[56] References Cited

U.S. PATENT DOCUMENTS

| | | |
|---|---|---|
| 1,229,312 | 6/1917 | Newhouse .................... 24/563 |
| 1,824,516 | 9/1931 | Tyvand . |
| 2,234,961 | 3/1941 | Canada . |
| 3,324,854 | 6/1967 | Weese . |
| 4,196,735 | 4/1980 | Ayer . |
| 4,314,568 | 2/1982 | Loving . |
| 4,586,924 | 5/1986 | Lanning . |
| 4,610,252 | 9/1986 | Catalano .................... 606/207 |
| 4,634,429 | 1/1987 | Schoettley .................. 604/115 |

*Primary Examiner*—David Isabella
*Assistant Examiner*—A. Zuttarelli
*Attorney, Agent, or Firm*—Dennison, Meserole, Pollack & Scheiner

[57] ABSTRACT

A stabilizer for blood vessels including a pair of diverging panels integrally joined at a bight portion which in turn defines a hinge between the panels. The panels have outer edges with extending legs for engagement with and manipulation of skin for the positioning and stabilizing of veins. The stabilizer includes linear forward edges and generally arcuate rear edges for use in varying situations.

12 Claims, 2 Drawing Sheets

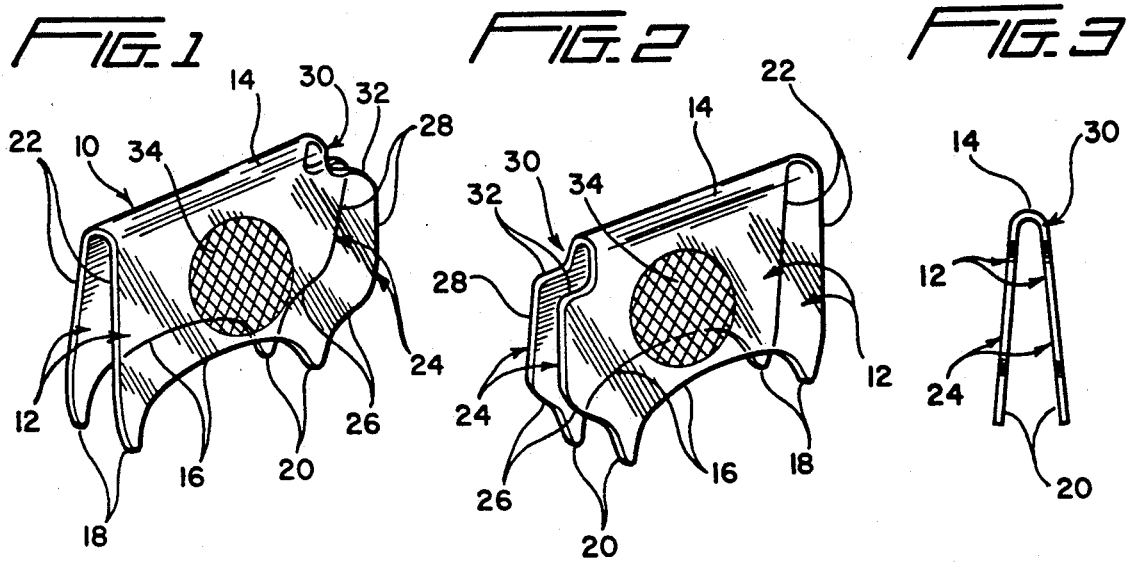
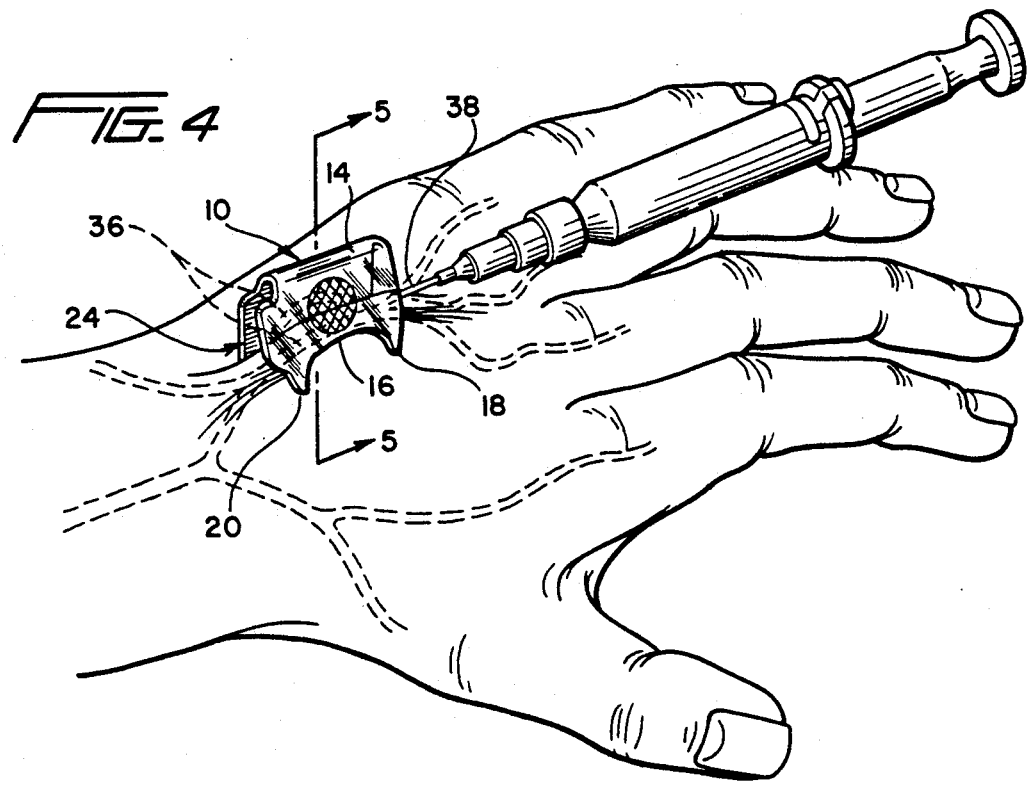
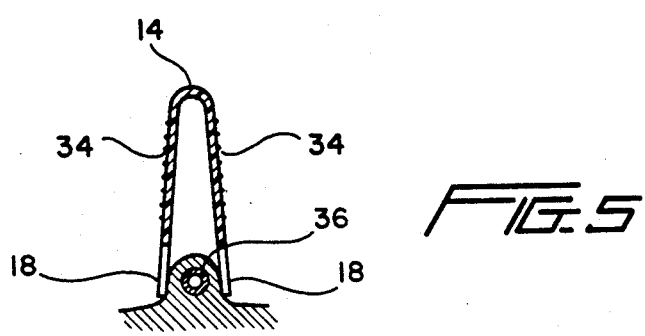

VEIN TENTER

BACKGROUND OF THE INVENTION

Venipuncture, whether for the drawing of blood or the introduction of medication, nourishment, and the like, necessitates a rather high degree of skill if the discomfiture to the patient and trauma to the skin and blood vessel, usually a vein, are to be minimized.

The major problems encountered in venipuncture arise from the inherent characteristics of veins with the difficulties varying from patient to patient, and in fact from vein to vein of the same patient. Such problems include the tendency of veins to move as the needle is being inserted or for that matter after the insertion of the needle, the tendency for some veins to collapse, while others curve or follow a circuitous path which makes proper needle alignment extremely difficult.

Frequently the caregiver will attempt some degree of vein manipulation or stabilization by direct finger contact. However the possibility of self puncturing makes such a procedure, in most circumstances, highly undesirable and potentially dangerous.

While various mechanical means have been devised for vein stabilization or positioning, such devices tend to be rather elaborate, requiring in many instances a positive mounting to the arm or the like. Known devices also tend to have limited utility insofar as being capable of accommodating, with a single instrument, the many circumstances which will normally arise with different patients as well as the particular veins which are to be positioned, stabilized and retained during venipuncture.

SUMMARY OF THE INVENTION

The present invention comprises a device which is easily manually manipulated by one hand to provide an effective means for preparing a vein or other blood vessel for venipuncture. Such preparation, depending upon the nature and location of the vein, will involve any or all of a series of actions utilizing the device in any of several orientations. The basic function of the device is to stabilize or hold a mobile vein in place. In conjunction therewith, the device can be used to straighten curving veins which might not otherwise be suitable for venipuncture; prevent "shadow" vein from collapsing or disappearing, thus making smaller veins more readily available; and increasing the diameter of a vein by lifting the skin lateral to the vein which in turn results in a larger effective vein diameter, also resulting in more rapid blood flow from the vein. The increased blood flow provides the related advantages of having fewer under filled tubes of blood and requiring less time for the actual drawing of the blood.

The stabilizing and straightening of the veins provides the additional benefit of decreasing incidents or probability of spearing through a vein with the resultant pain and unsightly extravasation of blood into the tissue around the vein.

While the device is particularly intended as an aid for venipuncture, it also facilitates subcutaneous and intracutaneous injections as it can be used to lift and bunch the skin, thereby increasing the depth of both the epidermis and dermis.

Another particularly significant feature of the stabilizer is the manner in which the device is adapted for direct manual manipulation, along with the versatility resulting therefrom as opposed to fixedly mounted units, wherein the fingers are positioned well above the plane of the needle. In this manner the problem of accidental needle stick is substantially decreased.

The tenter or stabilizer itself is preferably formed as a one piece unit of substantially rigid transparent synthetic resinous material. Structurally the stabilizer includes a pair of flat panels integrally connected along elongate inner edges by a bight portion which functions in the manner of a living hinge. The panels diverge outwardly at an acute angle relative to each other and terminate in outer edges, each including a forward leg and a rear leg.

The panels further include coplanar linear forward edges which define the forward edges of the forward legs, and rear edges which include arcuate or bulbous portions with the rear legs inwardly offset relative thereto along the outer edges of the panels.

The device is completed by a vein-accommodating recess defined in the integral bight portion at the upper extremities of the rear edges, and by opposed gripping areas defined in the outer surfaces of the panels between the bight and the outer edges.

The stabilizer is a compact inexpensive unit which, principally in view of the minimal costs involved both with regard to materials and actual formation of the device, is a disposable item, avoiding the necessity for re sterilization as required by the more complex and expensive devices which are intended for reuse.

The tapered nature of the item is significant in that the stabilizers are adapted for compact stacking or nesting, thus providing for substantial economies in both packaging and storage.

Other objects and advantages of the invention, including facilitating intracath insertion primarily due to a straightening of the vein course and enlarging the lumen, are considered to reside in the specifics of construction and manner of use of the invention as will be more fully hereinafter described.

BRIEF DESCRIPTION OF THE DRAWINGS

FIG. 1 is a perspective view of the stabilizer taken from the forward end thereof;

FIG. 2 is a perspective view of the stabilizer taken from the rear end thereof;

FIG. 3 is a rear end elevational view thereof;

FIG. 4 illustrates the stabilizer with the outer edges thereof manipulating a vein;

FIG. 5 is a cross-sectional detail taken substantially on a plane passing along line 5—5 in FIG. 4;

DESCRIPTION OF THE PREFERRED EMBODIMENTS

Figure 6:
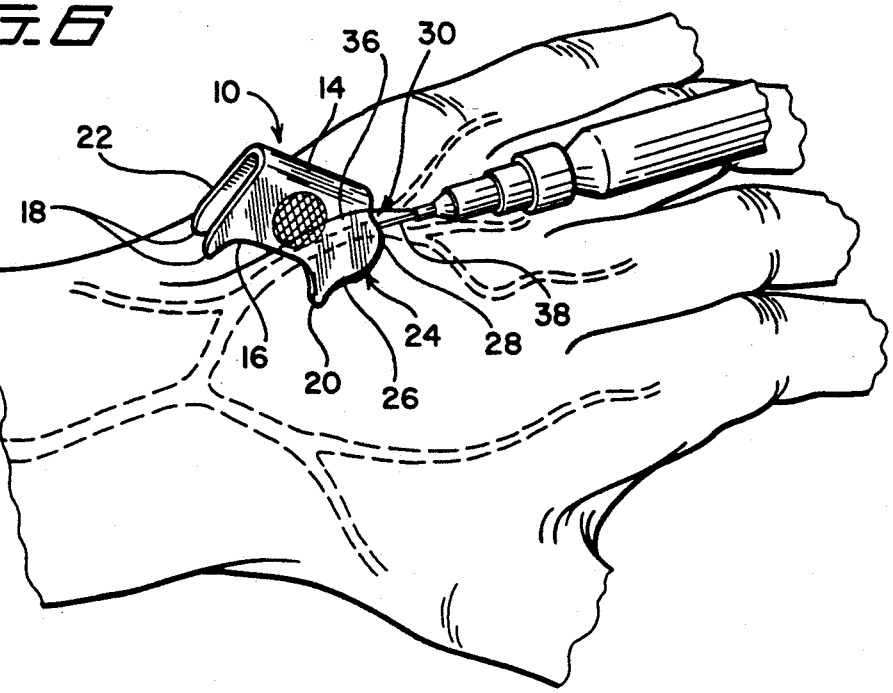
FIG. 6 illustrates the stabilizer with the rear edges thereof manipulating a vein.

Referring now more specifically to the drawings, and with particular reference to FIGS. 1-3, the tenter or stabilizer 10 is preferably formed from a single sheet of substantially rigid transparent synthetic resinous material folded to define a pair of duplicate flat panels 12 joined, along common inner edges, by an integral bight or bight portion 14.

The bight 14 is in the nature of a living hinge allowing for a selective hinging or pivoting of the panels 12 toward each other with the inherent nature of the material at the bight 14 allowing such movement and, upon release of pressure, returning the panels to their at rest or original position.

As noted in the drawings, the panels 12, prior to the application of compressive pressure thereto, diverge outwardly from the bight 14 at an acute angle to each other to terminate in laterally aligned coextensive outer or lower edges 16.

Each lower edge 16 is slightly concave and has forward and rear gripping legs 18 and 20 depending therefrom. These legs 18 and 20 are relatively narrow and taper to pointed ends about the thickness of a slightly dull pencil point.

The panels include coplanar linear or straight forward edges 22 which extend from the bight 14 for the full height of the corresponding panels 12 and the forward legs 18 thereof.

The rear edges 24 of the panels 12 are, in each case, of a generally arcuate configuration extending, along a convexly curved portion 26 from the inwardly offset rear legs 20 to about mid-height of the rear edge 24, and from there along a linear portion 28.

The integral hinge-defining bight 14 extends from the linear forward edges 22 for substantially the entire length of the stabilizer 10, terminating in inwardly spaced relation to the rear edges 24 to define a recess 30. Thus, it will be recognized that the rear edges 24, and in particular the linear upper portions 28 thereof, terminate in laterally spaced upper edges 32 with the actual spacing therebetween depending upon the particular depth of the recess 30.

The front and rear edges of each panel are straight with slightly rounded corners and otherwise smoothly formed to minimize skin trauma. Further, in order to facilitate finger manipulation of the stabilizer 10, it is preferred that the outer face of each panel 12 include a central slightly roughened or embossed grip enhancing area 34.

It will be appreciated that the actual size of the stabilizer can vary in accord with the requirements of the particular patient. For example, a smaller size stabilizer would be more practical with a child, while a substantially larger stabilizer would be more appropriate with a large adult. As one example of relative dimensions, the stabilizer can have a length of 2 inches, a height of 1.5 inches, a distance between the tip portions of the forward and rear legs of 1.375 inches, and a spacing between the panels at the tips of the legs of approximately 0.4 inches or 1 centimeter.

The manner of use of the stabilizer and the versatility thereof will be appreciated from the illustrated examples of FIGS. 4–8.

In FIGS. 4 and 5, the stabilizer 10 is positioned to generally tent over a curved vein 36 with thin points of the legs 18 and 20 of the opposed panels 12 engaged to the opposite sides thereof whereby, upon a compressing of the panels for pivotal movement of the outer edges 16 thereof toward each other, the vein is straightened and stabilized for proper reception of the needle 38 introduced into the vein between and just inside the two front legs 18. The narrow legs and thin points thereof avoid any tendency for the vein to disappear in the local area where the pressure is applied. As will be appreciated, the fingers holding the stabilizer 10 are well out of the path of insertion of the needle 38. Further, the transparent nature of the device allows full visibility during the procedure.

The divergent nature of the panels 12, as well as the slightly arcuate nature of each outer edge 16 between the corresponding legs 18 and 20 assist in accommodating the stabilizer 10 to various arm curvatures, for example when working with a vein that curves over the side of a patient's arm.

FIG. 6 illustrates use of the stabilizer 10 in areas of possible space limitations wherein the generally arcuate rear edges 24 comprise the means for straightening the vein path and stabilizing the vein. Utilized in this manner, the stabilizer can be backwardly tipped to raise the rear legs 20 out of contact with the skin with the vein 36 freely accommodated in the recess 30 to avoid any pressure directly on the top of the vein as might affect flow therethrough or access thereto. As will be recognized, the recess 30 allows for a positive seating and engagement of the arcuate or linear portions 26, 28 of the rear edges 24 to the opposite sides of the vein for a proper engagement and a subsequent straightening of the vein as the panels are manually compressed toward each other.

The arcuate portions 26 of the rear edges 24 also allow for a better fit of the stabilizer on the anterior elbow (antecubital area).

Figure 7:
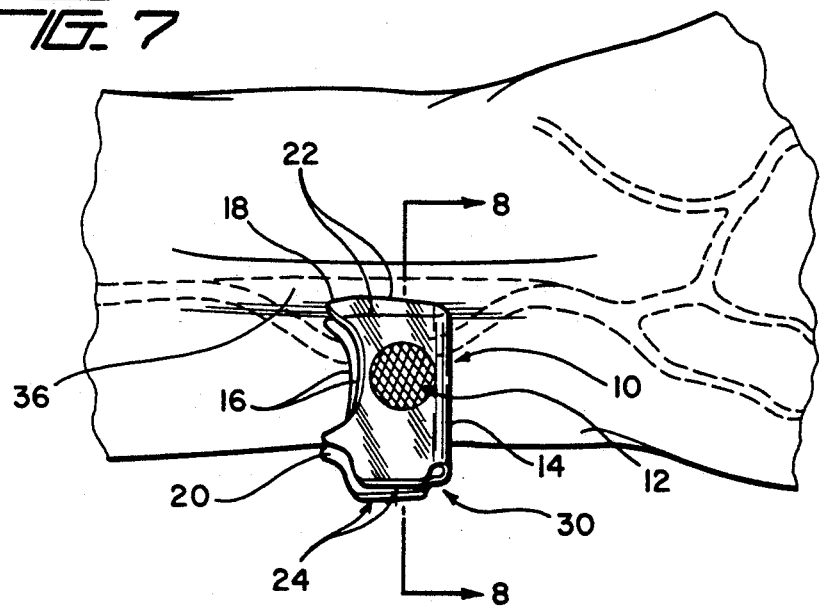
FIG. 7 illustrates the stabilizer with a forward edge positioned to manipulate a vein.
Figure 8:
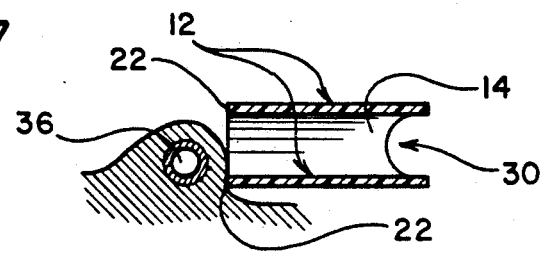
FIG. 8 is a cross sectional view taken substantially on a plane passing along line 8—8 in FIG. 7.

FIGS. 7 and 8 illustrate yet another manner of use of the stabilizer 10 wherein a vein path is straightened by a holding of the stabilizer 10 at approximately 30° to the skin surface and pushing against the curve of the vein 36 with one of the elongate straight forward edges 22 thus "bulldozing" the vein into position with continued pressure on the stabilizer retaining the vein as the puncturing procedure is preformed.

As with the previously described procedures, the hand holding and manipulating the stabilizer 10 is so positioned as to retain the fingers away from the actual puncture site, thus minimizing the possibility of accidental contact with the needle.

The vein stabilizer as described will find particular utility with those patients having "difficult veins" that is veins from which it is normally difficult to draw blood. Such situations obviously more frequently arise with regard to the elderly. The vein stabilizer will also of course find use with the general population, particularly in situations wherein access is desired to veins not normally considered usable because of curvatures therein, size and/or location For example, and as previously explained, the stabilizer is particularly effective in straightening curving veins and stabilizing the veins during venipuncture. The slightly concave nature of the outer edges 16 is also of significance in accommodating the stabilizer to body curvatures such as on a patient's arm. The device is also particularly adapted to prevent smaller veins from collapsing and disappearing, with the lifting of the skin lateral to the vein actually resulting in a larger effective vein diameter which enhances flow and blood withdrawal, while at the same time decreasing the possibility of spearing through the vein and the attendant problems resulting therefrom.

The foregoing is to be considered illustrative of the multiple features of, and advantages residing in, the stabilizer of the invention.

I claim:

1. A stabilizer for blood vessels comprising a pair of elongate flat panels adapted to be manually grasped and manipulated in one hand, said panels including elongate inner edges, hinge means joining said panels along said inner edges, said panels diverging from said hinge means at an acute angle relative to each other, each panel terminating in an elongate outer edge portion in lateral alignment with the elongate outer edge portion of the other panel remote from said hinge means, said hinge means resiliently retaining said panels with the outer edge portions laterally spaced from each other for selective manual lateral movement of said outer edge portions toward each other for engagement of skin of a patient and stabilization of a portion of a blood vessel positioned between said panels, said panels each having a forward edge and a rear edge extending between said joined inner edges and the respective outer edge portions, the forward edges being linear along their full extent and defining skin engaging and pushing means for directing lateral pressure against an adjacent blood vessel, each said rear edge, for a portion along their length, being convexly curved outward relative to the associated panel, said convexly curved portions of the rear edges being laterally opposed for engagement adjacent a portion of a blood vessel and stabilization of the portion of the blood vessel therebetween, each said panel having a grip area centrally thereof between said inner edge and said outer edge portion thereof and inwardly of said forward and rear edges thereof for selective manipulation of said outer edges, forward edges, and rear edges for blood vessel stabilization.

2. The stabilizer of claim 1 wherein said hinge means terminates longitudinally inward of said rear edges and defines an outwardly directed recess thereat for accommodation of a blood vessel through said recess upon engagement of the blood vessel by said opposed convexly curved portions of said rear edges and stabilization of the blood vessel without affecting flow therethrough.

3. The stabilizer of claim 2 wherein said outer edge portion of each panel includes an elongate outer edge, a forward gripping leg and a rear gripping leg integral and coplanar with the panel and extending from said outer edge thereof respectively adjacent said forward and rear edges.

4. The stabilizer of claim 3 wherein each forward leg is positioned immediately adjacent the forward edge of the associated panel and includes a forward edge portion aligned with said forward panel edge, each rear leg being spaced longitudinally inward along the outer edge and relative to the rear edge of the associated panel.

5. The stabilizer of claim 4 wherein said outer edge of each panel, between the forward and rear legs thereof, has a configuration slightly concave relative to the panel for facilitating accommodation to the body curvatures between said legs.

6. The stabilizer of claim 5 wherein said hinge means is integral with said panels, said panels and said hinge means being defined from a single sheet of material.

7. The stabilizer of claim 6 wherein said sheet of material is transparent.

8. A stabilizer for blood vessels comprising a pair of elongate flat panels adapted to be manually grasped and manipulated in one hand, said panels including elongate inner edges, hinge means joining said panels along said inner edges, said hinge means being integral with said panels, said panels and hinge means being defined from a single sheet of material, said panels diverging from said hinge means at an acute angle to each other, each panel, remote from said hinge means, terminating in an elongate outer edge in lateral alignment with the elongate outer edge of the other panel, said hinge means resiliently retaining said panels with said outer edges laterally spaced from each other for selective manual lateral movement of said outer edges toward each other for engagement of a skin surface of a patient and stabilization of a portion of a blood vessel positioned between said outer edges, said outer edge of each panel including a forward gripping leg and a rear gripping leg, said legs being integral with the panel and extending from said outer edge thereof, said legs along their full extent outward of said outer edge, being substantially coplanar with the panel, said legs on said outer edge of each panel being longitudinally spaced from each other therealong, said outer edge of each panel, between the forward and rear legs thereof, having a configuration slightly concave relative to the panel for facilitating accommodation to body curvatures between said legs.

9. The stabilizer of claim 8 wherein said panels each have a forward edge and a rear edge extending between the inner and outer edges thereof, each said forward edge being linear along its full extent and defining skin engaging and pushing means for directing lateral pressure against an adjacent blood vessel, each said rear edge, for a portion along its length, being convexly curved outward relative to the associated panel, the convexly curved portions being laterally opposed for engagement adjacent a portion of a blood vessel and stabilization of the portion of the blood vessel therebetween each said panel having a grip area centrally thereof inwardly of said inner and outer edges and inwardly of said forward and rear edges for selective manipulation of said outer edges, forward edges and rear edges for blood vessel stabilization.

10. The stabilizer of claim 9 wherein each forward leg is positioned immediately adjacent the forward edges of the associated panel and includes a forward edge portion aligned with said forward panel edge, each rear leg being spaced longitudinally inward along the outer edge and relative to the rear edge of the associated panel.

11. The stabilizer of claim 10 wherein said hinge means is integral with said panels, said panels and said hinge means being defined from a single sheet of material.

12. The stabilizer of claim 11 wherein said sheet of material is transparent.

* * * * *